(12) United States Patent
Rached et al.

US009528038B2

(10) Patent No.: US 9,528,038 B2
(45) Date of Patent: *Dec. 27, 2016

(54) COMPOSITIONS OF CHLORO-TRIFLUOROPROPENE AND HEXAFLUOROBUTENE

(71) Applicant: ARKEMA FRANCE, Colombes (FR)

(72) Inventors: Wissam Rached, Chaponost (FR); Laurent Abbas, Narberth, PA (US); Jean-Christophe Boutier, Oullins (FR)

(73) Assignee: ARKEMA FRANCE, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/861,073

(22) Filed: Sep. 22, 2015

(65) Prior Publication Data

US 2016/0009973 A1 Jan. 14, 2016

Related U.S. Application Data

(63) Continuation of application No. 13/988,362, filed as application No. PCT/IB2010/003428 on Nov. 25, 2010, now Pat. No. 9,157,018.

(51) Int. Cl.
| | | |
|---|---|---|
| C09K 5/04 | (2006.01) |
| C08J 9/14 | (2006.01) |
| C09K 3/30 | (2006.01) |
| C11D 7/50 | (2006.01) |
| C09K 3/00 | (2006.01) |
| C09K 5/10 | (2006.01) |
| A61K 8/04 | (2006.01) |
| A61K 8/69 | (2006.01) |
| A61K 9/12 | (2006.01) |
| A61K 47/06 | (2006.01) |
| A61Q 5/06 | (2006.01) |
| A61Q 13/00 | (2006.01) |
| A61Q 15/00 | (2006.01) |
| F28D 15/00 | (2006.01) |

(52) U.S. Cl.
CPC ............ *C09K 5/044* (2013.01); *A61K 8/046* (2013.01); *A61K 8/69* (2013.01); *A61K 9/124* (2013.01); *A61K 47/06* (2013.01); *A61Q 5/06* (2013.01); *A61Q 13/00* (2013.01); *A61Q 15/00* (2013.01); *C08J 9/144* (2013.01); *C08J 9/146* (2013.01); *C08J 9/149* (2013.01); *C09K 3/00* (2013.01); *C09K 3/30* (2013.01); *C09K 5/045* (2013.01); *C09K 5/10* (2013.01); *C11D 7/5018* (2013.01); *C11D 7/5054* (2013.01); *F28D 15/00* (2013.01); *C08J 2203/162* (2013.01); *C08J 2203/182* (2013.01); *C09K 2205/122* (2013.01); *C09K 2205/126* (2013.01); *C09K 2205/22* (2013.01); *C09K 2205/32* (2013.01)

(58) Field of Classification Search
CPC . C09K 5/045; C09K 2205/22; C09K 2205/43; F25B 39/02; F25B 45/00

USPC ............................ 252/67, 68, 69; 62/77, 119
See application file for complete search history.

(56) References Cited

U.S. PATENT DOCUMENTS

| | | | |
|---|---|---|---|
| 5,076,064 | A | 12/1991 | Kopko |
| 7,708,903 | B2 | 5/2010 | Sievert et al. |
| 7,972,524 | B2 | 7/2011 | Robin |
| 7,972,525 | B2 | 7/2011 | Robin |
| 8,262,924 | B2 | 9/2012 | Robin |
| 8,648,123 | B2 | 2/2014 | Van Horn et al. |
| 8,680,037 | B2 | 3/2014 | Robin |
| 8,821,749 | B2 | 9/2014 | Robin |
| 9,145,507 | B2 | 9/2015 | Rached |
| 9,157,018 | B2 | 10/2015 | Rached et al. |
| 9,267,066 | B2 | 2/2016 | Rached |
| 2007/0096051 | A1 | 5/2007 | Nappa et al. |
| 2007/0100009 | A1 | 5/2007 | Creazzo et al. |
| 2007/0100010 | A1 | 5/2007 | Creazzo et al. |
| 2007/0108403 | A1 | 5/2007 | Sievert et al. |
| 2007/0187639 | A1 | 8/2007 | Leck et al. |
| 2009/0143604 | A1 | 6/2009 | Nappa et al. |
| 2009/0204444 | A1 | 8/2009 | Tucker et al. |
| 2009/0302264 | A1 | 12/2009 | Serrano et al. |
| 2010/0056124 | A1 | 3/2010 | Keating et al. |
| 2010/0078585 | A1 | 4/2010 | Robin |
| 2010/0112328 | A1 | 5/2010 | Van Horn et al. |
| 2010/0134419 | A1 | 6/2010 | Fux et al. |
| 2010/0154419 | A1 | 6/2010 | Kontomaris |

(Continued)

FOREIGN PATENT DOCUMENTS

| | | | |
|---|---|---|---|
| JP | 2008-531836 A | 8/2008 |
| JP | 2010-522816 A | 7/2010 |

(Continued)

OTHER PUBLICATIONS

International Search Report (PCT/ISA/210) mailed on Aug. 11, 2011, by the European Patent Office as the International Searching Authority for International Application No. PCT/IB2010/003428.

(Continued)

*Primary Examiner* — Douglas McGinty

(74) *Attorney, Agent, or Firm* — Buchanan Ingersoll & Rooney P.C.

(57) ABSTRACT

Provided are compositions, preferably azeotrope or azeotrope-like compositions including 1,1,1,4,4,4-hexafluoro-2-butene and chlorotrifluoropropene, particularly 1-chloro-3,3,3-trifluoropropene (HCFO-1233zd), and uses thereof of the compositions. The composition may be a heat transfer composition. The composition may be a blowing agent composition. The composition may be a solvent composition. The composition may be a sprayable composition.

23 Claims, 1 Drawing Sheet

(56) References Cited

U.S. PATENT DOCUMENTS

| | | |
|---|---|---|
| 2010/0163776 A1 | 7/2010 | Robin |
| 2010/0216904 A1 | 8/2010 | Loh et al. |
| 2010/0243943 A1 | 9/2010 | Robin |
| 2010/0326095 A1 | 12/2010 | Van Horn et al. |
| 2011/0001080 A1 | 1/2011 | Van Horn et al. |
| 2011/0006248 A1 | 1/2011 | Van Horn et al. |
| 2011/0088418 A1 | 4/2011 | Kontomaris et al. |
| 2011/0144216 A1 | 6/2011 | Hulse et al. |
| 2011/0197604 A1 | 8/2011 | Minor et al. |
| 2011/0215273 A1 | 9/2011 | Uenveren et al. |
| 2011/0237844 A1 | 9/2011 | Tung et al. |
| 2011/0260093 A1 | 10/2011 | Robin |
| 2012/0004299 A1 | 1/2012 | Hulse et al. |
| 2012/0056124 A1 | 3/2012 | Robin |
| 2012/0085959 A1 | 4/2012 | Uenveren et al. |
| 2012/0117990 A1 | 5/2012 | Rached et al. |
| 2012/0119136 A1 | 5/2012 | Yana Motta et al. |
| 2013/0099154 A1 | 4/2013 | Boussand et al. |
| 2013/0247602 A1 | 9/2013 | Boutier et al. |
| 2013/0255284 A1 | 10/2013 | Rached |
| 2014/0048739 A1 | 2/2014 | Rached et al. |
| 2014/0083119 A1 | 3/2014 | Rached |
| 2014/0191153 A1 | 7/2014 | Yana Motta et al. |
| 2015/0096312 A1 | 4/2015 | Rached |
| 2015/0376485 A1 | 12/2015 | Rached |

FOREIGN PATENT DOCUMENTS

| | | |
|---|---|---|
| JP | 2010-532395 A | 10/2010 |
| WO | WO 2006/094303 A2 | 9/2006 |
| WO | WO 2007/002625 A2 | 1/2007 |
| WO | WO 2007/002703 A2 | 1/2007 |
| WO | WO 2007/053697 A2 | 5/2007 |
| WO | WO 2008/121776 A1 | 10/2008 |
| WO | WO 2008/134061 A2 | 11/2008 |
| WO | WO 2008/154612 A1 | 12/2008 |
| WO | WO 2009/085937 A1 | 7/2009 |
| WO | WO 2009/108547 A1 | 9/2009 |
| WO | WO 2009/114397 A2 | 9/2009 |
| WO | WO 2009/114398 A1 | 9/2009 |
| WO | WO 2010/055146 A2 | 5/2010 |
| WO | WO 2010/059677 A2 | 5/2010 |
| WO | WO 2010/062888 A2 | 6/2010 |
| WO | WO 2010/080467 A2 | 7/2010 |
| WO | WO 2010/100254 A1 | 9/2010 |
| WO | WO 2010/129461 A2 | 11/2010 |
| WO | WO 2010/141669 A1 | 12/2010 |
| WO | WO 2010141527 A1 | 12/2010 |
| WO | WO 2011/015737 A1 | 2/2011 |
| WO | WO 2011/084447 A2 | 7/2011 |
| WO | WO 2011/084553 A2 | 7/2011 |
| WO | WO 2011/137087 A1 | 11/2011 |
| WO | WO 2012/064477 A2 | 5/2012 |
| WO | WO 2012/069725 A1 | 5/2012 |
| WO | WO 2012/072910 A1 | 6/2012 |
| WO | WO 2013/004930 A1 | 1/2013 |

OTHER PUBLICATIONS

Morrison-Boyd, *Organic Chemistry*, 1973, p. 77, Table 3.1, Allyn and Bacon, Inc., Boston, MA, USA (3 pages).

Rached, Wissam, U.S. Appl. No. 14/844,583 entitled "Compositions of 2,4,4,4-Tetrafluorobut-1-ene and Cis-1,1,1,4,4,4-Hexafluorobut-2-ene," filed in the U.S. Patent and Trademark Office on Sep. 3, 2015.

Office Action issued by the European Patent office in EP 10 816 413.8, Apr. 28, 2014, 4 pages.

Kim, M.S., et al., "A Study to Determine the Existence of an Azeotropic R-22 'Drop-In' Substitute," NISTIR 5784, Mar. 1996, 50 pages, U.S. Department of Commerce.

Rached, Wissam, U.S. Appl. No. 14/990,546 entitled "Refrigerants Containing (E)-1,1,1,4,4,4-Hexafluorobut-2-ene," filed in the U.S. Patnet and Trademark Office on Jan. 7, 2016.

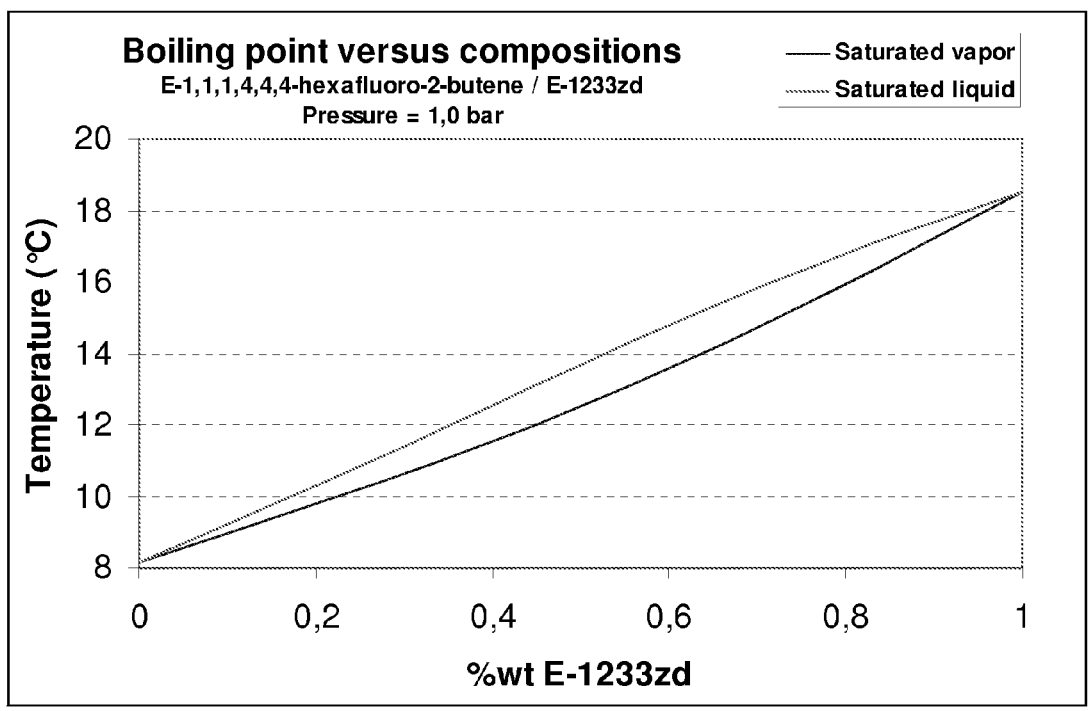

COMPOSITIONS OF CHLORO-TRIFLUOROPROPENE AND HEXAFLUOROBUTENE

CROSS REFERENCE TO RELATED APPLICATIONS

This application is a continuation of U.S. patent application Ser. No. 13/988,362, filed on Jun. 5, 2013, and issued as U.S. Pat. No. 9,157,018, which is a U.S. national stage entry of international application no. PCT/IB2010/003428, filed on Nov. 25, 2010. The entire contents of each of U.S. application Ser. No. 13/988,362 and international application no. PCT/IB2010/003428 are hereby incorporated by reference.

FIELD OF INVENTION

The present invention relates to compositions comprised of chloro-trifluoropropene, particularly 1-chloro-3,3,3-trifluoropropene (HCFO-1233zd) and hexafluorobutene.

BACKGROUND

Fluorocarbon based fluids have found widespread use in industry in a number of applications, including as refrigerants, aerosol propellants, blowing agents, heat transfer media, and gaseous dielectrics. Because of the suspected environmental problems associated with the use of some of these fluids, including the relatively high global warming potentials associated therewith, it is desirable to use fluids having low or even zero ozone depletion potential. Additionally, the use of single component fluids or azeotropic mixtures, which do not fractionate on boiling and evaporation, is desirable. However, the identification of new, environmentally safe, non-fractionating mixtures is complicated due to the fact that azeotrope formation is not readily predictable.

The industry is continually seeking new fluorocarbon based mixtures that offer alternatives, and are considered environmentally safer substitutes for CFCs and HCFCs.

The Montreal Protocol for the protection of the ozone layer, mandate the phase out of the use of chlorofluorocarbons (CFCs). Materials more "friendly" to the ozone layer, such as hydrofluorocarbons (HFCs) e.g. HFC-134a replaced chlorofluorocarbons. The latter compounds have proven to be greenhouse gases, causing global warming and were regulated by the Kyoto Protocol on Climate Change. The emerging replacement materials, hydrofluoropropenes, were shown to be environmentally acceptable i.e. have zero ozone depletion potential (ODP) and acceptable low GWP.

WO 2007/002625 disclosed compositions comprising at least one fluoroolefin having from three to six atoms of carbon which can be used as heat transfer fluid. Tetrafluoropropenes, chlorotrifluoropropenes and pentafluoropropenes are considered as preferred.

WO 2007/002703 described the use of these fluoropropenes as blowing agent in the manufacture of foams (polyurethanes and thermoplastics).

WO 2008/134061 describes azeotrope or azeotrope-like compositions of Z-1,1,1,4,4,4-hexafluoro-2-butene (Z-FC-1336mzz) with methyl formate.

WO 2008/154612 describes azeotrope or azeotrope-like compositions of E-1,1,1,4,4,4-hexafluoro-2-butene (Z-FC-1336mzz) with methyl formate.

The object of the present invention is to provide novel compositions that can serve as refrigerants, heat transfer fluids, blowing agents, solvents, aerosol, that provide unique characteristics to meet the demands of low or zero ozone depletion potential and lower global warming potential as compared to the current HFCs.

BRIEF DESCRIPTION OF THE DRAWING

FIG. 1 is a graph of boiling point versus % wt. of E-1233zd in a mixture of E-1233zd and E-1,1,1,4,4,4-hexafluoro-2-butene.

DETAILED DESCRIPTION

The present inventors have developed a composition comprising 1,1,1,4,4,4-hexafluoro-2-butene and at least one chlorotrifluoropropene that help to satisfy the continuing need for alternatives to CFCs and HCFCs.

The composition comprises preferably from 1 to 99% by weight of 1,1,1,4,4,4-hexafluoro-2-butene and 1 to 99% by weight of chlorotrifluoropropene(s).

The composition comprises more preferably from 60 to 99% by weight of 1,1,1,4,4,4-hexafluoro-2-butene and 1 to 40% by weight of chlorotrifluoropropene(s). Composition comprising 1 to 30% by weight of 1,1,1,4,4,4-hexafluoro-2-butene and 70 to 99% by weight of chlorotrifluoropropene(s) is also more preferred. According to the present invention, the E-1,1,1,4,4,4-hexafluoro-2-butene (i.e. the trans isomer of 1,1,1,4,4,4-hexafluoro-2-butene) is preferred.

As chlorotrifluoropropene, 1-chloro-3,3,3-trifluoropropene (HCFO-1233zd) and 2-chloro-3,3,3-trifluoropropene (HCFO-1233xf) are preferred.

According to the present invention, the 1-chloro-3,3,3-trifluoropropene is preferred. Preferably more than 90% by weight of 1-chloro-3,3,3-trifluoropropene present in the composition is trans isomer, E-1-chloro-3,3,3-trifluoropropene.

The preferred compositions of the invention tend both to be low- to non-flammable and to exhibit relatively low global warming potentials ("GWPs"). Accordingly, applicants have recognized that such compositions can be used to great advantage in a number of applications, including as replacements for CFCs, HCFCs, and HFCs (such as CFC-114, HCFC-23, HFC-134a, HFC-245fa, HFC-365mfc) in refrigerant, aerosol, and other applications.

Additionally, applicant has recognized surprisingly that azeotrope or azeotrope-like compositions of 1,1,1,4,4,4-hexafluoro-2-butene and at least one chlorotrifluoropropene can be formed.

According to one preferred embodiment of the present invention, the azeotrope or azeotrope-like compositions comprised of E-1-chloro-3,3,3-trifluoropropene and E-1,1,1,4,4,4-hexafluoro-2-butene.

In addition, applicants have recognized that the azeotrope-like compositions of the present invention exhibit properties that make them advantageous for use as, or in, refrigerant compositions and in foam blowing agents. Accordingly, in yet other embodiments, the present invention provides heat transfer compositions and/or blowing agents, aerosol and solvents comprising an azeotrope or azeotrope-like composition of 1,1,1,4,4,4-hexafluoro-2-butene and at least one chlorotrifluoropropene, preferably of azeotrope or azeotrope-like compositions comprised of E-1-chloro-3,3,3-trifluoropropene and E-1,1,1,4,4,4-hexafluoro-2-butene.

Azeotrope-Like Compositions

As used herein, the term "azeotrope-like" is intended in its broad sense to include both compositions that are strictly azeotropic and compositions that behave like azeotropic mixtures. From fundamental principles, the thermodynamic state of a fluid is defined by pressure, temperature, liquid composition, and vapor composition. An azeotropic mixture is a system of two or more components in which the liquid composition and vapor composition are equal at the stated pressure and temperature. In practice, this means that the components of an azeotropic mixture are constant boiling and cannot be separated during a phase change.

The azeotrope-like compositions of the present invention may include additional components that do not form new azeotrope-like systems, or additional components that are not in the first distillation cut. The first distillation cut is the first cut taken after the distillation column displays steady state operation under total reflux conditions. One way to determine whether the addition of a component forms a new azeotrope-like system so as to be outside of this invention is to distill a sample of the composition with the component under conditions that would be expected to separate a non-azeotropic mixture into its separate components. If the mixture containing the additional component is non-azeotrope-like, the additional component will fractionate from the azeotrope-like components. If the mixture is azeotrope-like, some finite amount of a first distillation cut will be obtained that contains all of the mixture components that is constant boiling or behaves as a single substance.

It follows from this that another characteristic of azeotrope-like compositions is that there is a range of compositions containing the same components in varying proportions that are azeotrope-like or constant boiling. All such compositions are intended to be covered by the terms "azeotrope-like" and "constant boiling". As an example, it is well known that at differing pressures, the composition of a given azeotrope will vary at least slightly, as does the boiling point of the composition. Thus, an azeotrope of A and B represents a unique type of relationship, but with a variable composition depending on temperature and/or pressure. It follows that, for azeotrope-like compositions, there is a range of compositions containing the same components in varying proportions that are azeotrope-like. All such compositions are intended to be covered by the term azeotrope-like as used herein.

According to certain preferred embodiments, the azeotrope or azeotrope-like compositions of the present invention consist essentially of, effective azeotrope or azeotrope-like amounts of 1,1,1,4,4,4-hexafluoro-2-butene and at least one chlorotrifluoropropene. The term "effective azeotrope-like amounts" as used herein refers to the amount of each component that upon combination with the other components, results in the formation of an azeotrope-like composition of the present invention. Preferably, the present azeotrope-like compositions consist essentially of, from about 1. to about 99 weight percent of E-1,1,1,4,4,4-hexafluoro-2-butene and from about 1. to about 99 weight percent of E-1-chloro-3,3,3-trifluoropropene. Advantageously, the present azeotrope-like compositions preferably consist essentially of, from about 60 to about 99 weight percent of E-1,1,1,4,4,4-hexafluoro-2-butene and from about 1 to about 40 weight percent of E-1-chloro-3,3,3-trifluoropropene.

Azeotrope-like compositions preferably consisting essentially of, from about 1 to about 30 weight percent of E-1,1,1,4,4,4-hexafluoro-2-butene and from about 70 to about 99 weight percent of E-1-chloro-3,3,3-trifluoropropene is also preferred.

The azeotrope-like compositions of the present invention can be produced by combining an effective azeotrope or azeotrope-like amounts of 1,1,1,4,4,4-hexafluoro-2-butene and chlorotrifluoropropene. For example, E-1,1,1,4,4,4-hexafluoro-2-butene and E-1-chloro-3,3,3-trifluoropropene can be mixed, blended, or otherwise contacted by hand and/or by machine, as part of a batch or continuous reaction and/or process, or via combinations of two or more such steps.

Composition Additives

The compositions, azeotrope or azeotrope-like compositions of the present invention may further include any of a variety of optional additives including stabilizers, metal passivators, corrosion inhibitors, and the like.

In certain preferred embodiments, the compositions of the present invention further comprise a lubricant. Any of a variety of conventional lubricants may be used in the compositions of the present invention. An important requirement for the lubricant is that, when in use in a refrigerant system, there must be sufficient lubricant returning to the compressor of the system such that the compressor is lubricated. Thus, suitability of a lubricant for any given system is determined partly by the refrigerant/lubricant characteristics and partly by the characteristics of the system in which it is intended to be used. Examples of suitable lubricants include mineral oil, alkyl benzenes, polyol esters, including polyalkylene glycols, PAG oil, polyvinyl ethers oil and the like. Mineral oil, which comprises paraffin oil or naphthenic oil, is commercially available. Commercially available mineral oils include Witco LP 250 (registered trademark) from Witco, Zerol 300 (registered trademark) from Shrieve Chemical, Sunisco 3GS from Witco, and Calumet R015 from Calumet. Commercially available alkyl benzene lubricants include Zerol 150 (registered trademark). Commercially available esters include neopentyl glycol dipelargonate which is available as Emery 2917 (registered trademark) and Hatcol 2370 (registered trademark). Other useful esters include phosphate esters, dibasic acid esters, and fluoroesters. Preferred lubricants include polyalkylene glycols and esters. Certain more preferred lubricants include polyalkylene glycols.

Uses of the Compositions

The present compositions have utility in a wide range of applications. For example, one embodiment of the present invention relates to heat transfer fluid compositions comprising the present compositions.

The heat transfer fluid compositions of the present invention may be used in any of a wide variety of refrigeration systems including air-conditioning, refrigeration, heat-pump in particular with heat pumps operating at condensation temperature up to 140° C., chiller, HVAC systems, centrifugal compressors, Organic Rankin cycle for power and electricity production and the like.

Heat Pumps and Organic Rankin cycle can use renewable energy sources like solar, geothermal or heat rejection from industrial process).

In certain preferred embodiments, the compositions of the present invention are used in refrigeration systems originally designed for use with an HCFC refrigerant, such as, for example, HCFC-123. The preferred compositions of the present invention tend to exhibit many of the desirable characteristics of HCFC-123 and other HFC refrigerants, including a GWP that is as low, or lower than that of conventional HFC refrigerants and a capacity that is as high or higher than such refrigerants. In addition, the relatively constant boiling nature of the compositions of the present invention makes them even more desirable than certain conventional HFCs for use as refrigerants in many applications.

Azeotrope-like composition comprising, preferably consisting essentially of from 1 to 85% by weight of E-1,1,1,4,4,4-hexafluoro-2-butene and 15 to 99% by weight of E-1-chloro-3,3,3-trifluoropropene, is useful in Organic Rankin Cycle, in replacement of 1,1,1,3,3-pentafluoropropane (HFC-245fa) and in replacement of HCFC-123 (2,2-dichloro-1,1,1-trifluoroethane). This azeotrope-like composition is particularly useful in Organic Rankin Cycle.

Azeotrope-like composition comprising, preferably consisting essentially of from 50 to 70% by weight of E-1,1,1,4,4,4-hexafluoro-2-butene and 30 to 50% by weight of E-1-chloro-3,3,3-trifluoropropene, is particularly useful in air conditioning and more particularly in replacing HCFC-123 (2,2-dichloro-1,1,1-trifluoroethane) in centrifugal compressors of air conditioner or heat pumps.

Azeotrope-like composition comprising, preferably consisting essentially of from 1 to 25% by weight of E-1,1,1,4,4,4-hexafluoro-2-butene and 75 to 99% by weight of E-1-chloro-3,3,3-trifluoropropene, is particularly useful in replacing 1,1,1,3,3-pentafluoropropane (HFC-245fa) in centrifugal compressors of air conditioner or heat pumps.

Azeotrope-like composition comprising, preferably consisting essentially of from 1 to 45% by weight of E-1,1,1,4,4,4-hexafluoro-2-butene and 55 to 99% by weight of E-1-chloro-3,3,3-trifluoropropene, is particularly useful in replacing 1,1,1,3,3-pentafluoropropane (HFC-245fa), preferably for heat pumps, more preferably high temperature heat pump.

In certain other preferred embodiments, the present compositions are used in refrigeration systems originally designed for use with a CFC-refrigerant. Preferred refrigeration compositions of the present invention may be used in refrigeration systems containing a lubricant used conventionally with CFC-refrigerants, such as mineral oils, silicone oils, polyalkylene glycol oils, and the like, or may be used with other lubricants traditionally used with HFC refrigerants. As used herein the term "refrigeration system" refers generally to any system or apparatus, or any part or portion of such a system or apparatus, which employs a refrigerant to provide cooling. Such refrigeration systems include, for example, air conditioners, electric refrigerators, chillers, transport refrigeration systems, commercial refrigeration systems and the like.

Any of a wide range of methods for introducing the present refrigerant compositions to a refrigeration system can be used in the present invention. For example, one method comprises attaching a refrigerant container to the low-pressure side of a refrigeration system and turning on the refrigeration system compressor to pull the refrigerant into the system. In such embodiments, the refrigerant container may be placed on a scale such that the amount of refrigerant composition entering the system can be monitored. When a desired amount of refrigerant composition has been introduced into the system, charging is stopped. Alternatively, a wide range of charging tools, known to those of skill in the art, is commercially available. Accordingly, in light of the above disclosure, those of skill in the art will be readily able to introduce the refrigerant compositions of the present invention into refrigeration systems according to the present invention without undue experimentation.

According to certain other embodiments, the present invention provides refrigeration systems comprising a refrigerant of the present invention and methods of producing heating or cooling by condensing and/or evaporating a composition of the present invention. In certain preferred embodiments, the methods for cooling an article according to the present invention comprise condensing a refrigerant composition comprising an azeotrope-like composition of the present invention and thereafter evaporating said refrigerant composition in the vicinity of the article to be cooled. Certain preferred methods for heating an article comprise condensing a refrigerant composition comprising an azeotrope-like composition of the present invention in the vicinity of the article to be heated and thereafter evaporating said refrigerant composition.

Heat exchangers used in the heat transfer systems may be of any type. Typical heat exchangers include parallel or co-current flow, counterflow, cross-flow. Preferably, heat exchangers used with the heat transfer compositions of the present invention are counterflow, counterflow-like, or crossflow.

In another embodiment, the azeotrope-like compositions of this invention may be used as propellants in sprayable compositions, either alone or in combination with known propellants. The propellant composition comprises, more preferably consists essentially of, and, even more preferably, consists of the azeotrope-like compositions of the invention. The active ingredient to be sprayed together with inert ingredients, solvents, and other materials may also be present in the sprayable mixture. Preferably, the sprayable composition is an aerosol. Suitable active materials to be sprayed include, without limitation, cosmetic materials such as deodorants, perfumes, hair sprays, cleansers, and polishing agents as well as medicinal materials such as anti-asthma and anti-halitosis medications.

Yet another embodiment of the present invention relates to a blowing agent comprising one or more azeotrope-like compositions of the invention. In other embodiments, the invention provides foamable compositions, and preferably polyurethane and polyisocyanurate foam compositions, and methods of preparing foams. In such foam embodiments, one or more of the present azeotrope-like compositions are included as a blowing agent in a foamable composition, which composition preferably includes one or more additional components capable of reacting and foaming under the proper conditions to form a foam or cellular structure, as is well known in the art. Any of the methods well known in the art, may be used or adapted for use in accordance with the foam embodiments of the present invention.

Another embodiment of this invention relates to a process for preparing a foamed thermoplastic product as follows: Prepare a foamable polymer composition by blending together components comprising foamable polymer composition in any order. Typically, a foamable polymer composition is prepared by plasticizing a polymer resin and then blending in components of a blowing agent composition at an initial pressure. A common process of plasticizing a polymer resin is heat plasticization, which involves heating a polymer resin enough to soften it sufficiently to blend in a blowing agent composition. Generally, heat plasticization involves heating a thermoplastic polymer resin to or near to its glass transition temperature (Tg), or melt temperature (Tm) for crystalline polymers. Other uses of the present azeotrope-like compositions include use as solvents, cleaning agents, and the like. Examples include vapor degreasing, precision cleaning, electronics cleaning, drying cleaning, solvent etching cleaning, carrier solvents for depositing lubricants and release agents, and other solvent or surface treatment. Those of skill in the art will be readily able to adapt the present compositions for use in such applications without undue experimentation.

Example 1

Azeotrope-Like Compositions

A vacuum cell equipped with a saphir tube is heated at 60° C. using an oil bath. Once temperature equilibrium is reached, the cell is charged with E-1-chloro-3,3,3-trifluoropropene and the pressure at which equilibrium is reached is recorded. An amount of E-1,1,1,4,4,4-hexafluoro-2-butene is introduced in the cell and the content is mixed in order to accelerate equilibrium. At equilibrium, a very small quantity of a sample is taken from the gaseous phase as well as the liquid phase to be analyzed by gas chromatography with thermal detector.

Equilibrium data gathered with different compositions of E-1-chloro-3,3,3-trifluoropropene and E-1,1,1,4,4,4-hexafluoro-2-butene, have then be converted to pressure at boiling point of each composition.

From greater than about 0 to 99 weight percent E-1-chloro-3,3,3-trifluoropropene the boiling point of the composition changed by 1.5° C. or less. The compositions exhibit azeotrope-like properties over this range.

Example 2

Compression System Applications

Technical Background

The RK-Soave equation of state has been used to calculate gas density, enthalpy and entropy data and has been used to predict latent heat of vaporization and vapor equilibrium data for the mixtures of interest.

The basic properties required by this equation (critical temperature, critical pressure and vapor pressures versus temperatures) were measured by using a static cell.

The acentric factor of each pure product was calculated from measurements of the vapor pressure curves.

Ideal gas heat capacity data were also estimated using Benson group contribution method. All of these estimation techniques are described in the text "The Properties of Gases & Liquids" by Bruce E. Poling, John M. Prausnitz, Johan P. O'Connell, 5th edition, published McGraw-Hill.

Interaction parameters between pair of pure products were obtained from vapor liquid equilibrium measurements.

The vapor liquid equilibrium results of E-1-chloro-3,3,3-trifluoropropene and E-1,1,1,4,4,4-hexafluoro-2-butene were described in the previous paragraph.

The thermodynamic model using RK-Soave equation is used for cycle properties calculations. These cycles can include heat exchangers (evaporators, condensers . . . ), internal heat exchangers, heater, expansion valves, compressors, liquid pumps and turbines.

The coefficient of performance (COP) is the ratio of the useful energy delivered by the system divided by the energy consumption.

The Lorenz coefficient of performance is a reference value. It is calculated in function of the system temperatures and it is used for fluid performances comparison.

The COPLorenz is defined as follow:
(Temperature unit: K)

$$T_{medium}^{condenser} = T_{inlet}^{condenser} - T_{outlet}^{condenser} \quad (1)$$

$$T_{medium}^{evaporator} = T_{outlet}^{evaporator} - T_{inlet}^{evaporator} \quad (1)$$

COPLorenz for air conditioning or refrigeration is defined as follows $$COPlorenz = \frac{T_{medium}^{evaporator}}{T_{medium}^{condenser} - T_{medium}^{evaporator}} \quad (4)$$

COPLorenz for heat pump is defined as follows $$COPlorenz = \frac{T_{medium}^{condenser}}{T_{medium}^{condenser} - T_{medium}^{evaporator}} \quad (5)$$

For each composition, the Lorenz coefficient of performance is calculated in function of temperatures. The % COP/COPLorenz is the percentage ratio of the system COP over the Lorenz COP.

For organic Rankin cycle, the efficiency is the ratio of the energy available at the turbine outlet divided by the evaporator energy consumption.

Air Conditioner and Air Conditioner Using Centrifugal Compressors:

The system is operating with 5° C. superheat, an internal heat exchanger and a centrifugal compressor with an isoentropic efficiency is 81%.

The composition performances are shown in table 1 & 2. The composition of each products (HCFO-1233zd(E), (2E)-1,1,1,4,4,4-hexafluorobut-2-ene) are in weight percentage.

For HFC-245fa substitution, the most preferred compositions are between 75 and 99% wt of HFO-1233zd.

For HCFC-123 substitution, the most preferred compositions are between 30 and 50% wt of HFO-1233zd.

For these compositions, the speed of sound for the blend is equivalent to the HCFC-123 or HFC-245fa speed of sound.

TABLE 1

| HFO-1233zd | (2E)-1,1,1,4,4,4-hexafluorobut-2-ene | Evaporating temperature (° C.) | Compressor outlet temperature (° C.) | Condensation tempeature (° C.) | Expension valvae inlet temperature (° C.) | Low pressure (bar) | High presure (bar) | Pressure ratio (p/p) | % Volumetric capacity | Molar mass (g) | speed of sound (m/s) | % COP/COPLorenz |
|---|---|---|---|---|---|---|---|---|---|---|---|---|
| HFC-245fa | | 5 | 47 | 40 | 37 | 0.6 | 2.5 | 3.8 | 630 | 134 | 134 | 71 |
| 75 | 25 | 5 | 48 | 40 | 37 | 0.6 | 2.4 | 3.9 | 593 | 139 | 132 | 69 |
| 80 | 20 | 5 | 49 | 40 | 37 | 0.6 | 2.4 | 3.8 | 584 | 138 | 133 | 69 |
| 85 | 15 | 5 | 49 | 40 | 37 | 0.6 | 2.3 | 3.8 | 576 | 136 | 134 | 69 |
| 90 | 10 | 5 | 50 | 40 | 37 | 0.6 | 2.3 | 3.8 | 568 | 134 | 135 | 70 |

TABLE 2

| HFO-1233zd | (2E)-1,1,1,4,4,4-hexafluorobut-2-ene | Evaporating temperature (° C.) | Compressor outlet temperature (° C.) | Condensation tempearture (° C.) | Expension valave inlet temperature (° C.) | Low presure (bar) | High presure (bar) | Pressure ratio (p/p) | % Volumetric capacity | % COP/ COPLorenz | Molar mass (g) | speed of sound (m/s) |
|---|---|---|---|---|---|---|---|---|---|---|---|---|
| HCFC-123 | | 5 | 50 | 40 | 37 | 0.4 | 1.5 | 3.8 | 100 | 72 | 153 | 127 |
| 0 | 100 | 5 | 40 | 40 | 37 | 0.9 | 3.2 | 3.6 | 189 | 68 | 164 | 118 |
| 10 | 90 | 5 | 41 | 40 | 37 | 0.9 | 3.1 | 3.6 | 185 | 68 | 161 | 120 |
| 20 | 80 | 5 | 42 | 40 | 37 | 0.8 | 3.0 | 3.6 | 181 | 68 | 157 | 122 |
| 30 | 70 | 5 | 43 | 40 | 37 | 0.8 | 2.9 | 3.7 | 176 | 68 | 154 | 124 |
| 33 | 67 | 5 | 44 | 40 | 37 | 0.8 | 2.9 | 3.7 | 175 | 69 | 153 | 125 |
| 40 | 60 | 5 | 45 | 40 | 37 | 0.8 | 2.8 | 3.7 | 171 | 69 | 151 | 126 |
| 50 | 50 | 5 | 46 | 40 | 37 | 0.7 | 2.7 | 3.7 | 166 | 69 | 147 | 128 |
| 60 | 40 | 5 | 47 | 40 | 37 | 0.7 | 2.6 | 3.7 | 160 | 69 | 144 | 130 |
| 70 | 30 | 5 | 48 | 40 | 37 | 0.7 | 2.5 | 3.7 | 154 | 70 | 141 | 131 |
| 80 | 20 | 5 | 49 | 40 | 37 | 0.6 | 2.4 | 3.7 | 148 | 70 | 137 | 133 |
| 90 | 10 | 5 | 49 | 40 | 37 | 0.6 | 2.3 | 3.8 | 142 | 70 | 134 | 135 |
| 100 | 0 | 5 | 50 | 40 | 37 | 0.6 | 2.2 | 3.8 | 136 | 70 | 131 | 136 |

Heat Pump and High Temperature Heat Pump

The system is operating with 5° C. superheat, an internal heat exchanger and a screw compressor.

The compressor isoentropic efficiency is calculated in function of the compression ratio according to the following formula.

$$\eta_{isen} = a - b(\tau - c)^2 - \frac{d}{\tau - e}$$

The a, b, c, d and e constant are found using data published in the Handbook of air conditioning and refrigeration, page 11.52.

The composition performances are shown in table 3. The composition of each products (HCFO-1233zd(E), (2E)-1,1,1,4,4,4-hexafluorobut-2-ene) are in weight percentage.

TABLE 3

| HFO-1233zd | (2E)-1,1,1,4,4,4-hexafluorobut-2-ene | Evaporating temperature (° C.) | Compressor outlet temperature (° C.) | Condensation tempearture (° C.) | Expension valave inlet temperature (° C.) | Low presure (bar) | High presure (bar) | Pressure ratio (p/p) | isentropic efficiency | % Volumetric capacity | % COP/ COPLorenz | Critical temperature |
|---|---|---|---|---|---|---|---|---|---|---|---|---|
| HFC-245fa | | 30 | 93 | 90 | 87 | 1.7 | 10.1 | 5.8 | 74 | 100 | 58 | 154 |
| 55 | 45 | 30 | 91 | 90 | 87 | 1.9 | 10.2 | 5.4 | 76 | 97 | 57 | 153 |
| 65 | 35 | 30 | 92 | 90 | 87 | 1.8 | 9.8 | 5.5 | 76 | 96 | 58 | 157 |
| 75 | 25 | 30 | 93 | 90 | 87 | 1.7 | 9.4 | 5.4 | 76 | 94 | 59 | 160 |
| 85 | 15 | 30 | 94 | 90 | 87 | 1.6 | 8.9 | 5.4 | 76 | 92 | 60 | 163 |
| 95 | 5 | 30 | 95 | 90 | 87 | 1.6 | 8.6 | 5.4 | 76 | 90 | 61 | 166 |

Organic Rankin Cycle

The system includes a turbine. The turbine can be coupled to a generator on order to produce electricity.

The composition performances are shown in table 4 & 5. The composition of each products (HCFO-1233zd(E), (2E)-1,1,1,4,4,4-hexafluorobut-2-ene) are in weight percentage.

TABLE 4

90° C. evaporating temperature and 20° C. condensing temperature

| | | Evaporating temperature (° C.) | Condensation tempearture (° C.) | Turbine outlet temperature (° C.) | Pump outlet temperature (° C.) | Heater inlet temperature (° C.) | Low pressure (bar) | High presure (bar) | Pressure ratio (p/p) | efficciency |
|---|---|---|---|---|---|---|---|---|---|---|
| HCFC-114 | | 90 | 20 | 38 | 20 | 33 | 1.8 | 11.5 | 6.3 | 0.17 |
| HFO-1233zd | (2E)-1,1,1,4,4,4-hexafluorobut-2-ene | | | | | | | | | |
| 0 | 100 | 90 | 20 | 41 | 20 | 35 | 1.6 | 12.1 | 7.6 | 0.17 |
| 5 | 95 | 90 | 20 | 41 | 20 | 35 | 1.6 | 12.0 | 7.6 | 0.17 |
| 15 | 85 | 90 | 20 | 40 | 20 | 34 | 1.5 | 11.6 | 7.6 | 0.17 |
| 25 | 75 | 90 | 20 | 39 | 20 | 33 | 1.5 | 11.3 | 7.6 | 0.17 |
| 35 | 65 | 90 | 20 | 39 | 20 | 32 | 1.4 | 10.9 | 7.6 | 0.17 |
| 45 | 55 | 90 | 20 | 38 | 20 | 31 | 1.4 | 10.6 | 7.6 | 0.17 |
| 55 | 45 | 90 | 20 | 37 | 20 | 30 | 1.3 | 10.2 | 7.7 | 0.17 |
| 65 | 35 | 90 | 20 | 36 | 20 | 29 | 1.3 | 9.8 | 7.7 | 0.17 |
| 75 | 25 | 90 | 20 | 35 | 20 | 29 | 1.2 | 9.4 | 7.7 | 0.17 |
| 85 | 15 | 90 | 20 | 33 | 20 | 28 | 1.2 | 8.9 | 7.7 | 0.17 |
| 95 | 5 | 90 | 20 | 32 | 20 | 27 | 1.1 | 8.6 | 7.8 | 0.17 |
| 100 | 0 | 90 | 20 | 31 | 20 | 26 | 1.1 | 8.4 | 7.8 | 0.17 |

TABLE 5

120° C. evaporating temperature and 20° C. condensing temperature

| | | Evaporating temperature (° C.) | Condensation tempearture (° C.) | Turbine outlet temperature (° C.) | Pump outlet temperature (° C.) | Heater inlet temperature (° C.) | Low pressure (bar) | High presure (bar) | Pressure ratio (p/p) | efficciency |
|---|---|---|---|---|---|---|---|---|---|---|
| HCFC-114 | | 120 | 20 | 42 | 21 | 36 | 1.8 | 20.8 | 11.4 | 0.21 |
| HFO-1233zd | (2E)-1,1,1,4,4,4-hexafluorobut-2-ene | | | | | | | | | |
| 15 | 85 | 120 | 20 | 45 | 21 | 37 | 1.5 | 21.5 | 14.1 | 0.21 |
| 25 | 75 | 120 | 20 | 44 | 21 | 36 | 1.5 | 20.9 | 14.1 | 0.21 |
| 35 | 65 | 120 | 20 | 44 | 21 | 36 | 1.4 | 20.3 | 14.1 | 0.21 |
| 45 | 55 | 120 | 20 | 43 | 21 | 35 | 1.4 | 19.6 | 14.2 | 0.21 |
| 55 | 45 | 120 | 20 | 42 | 21 | 34 | 1.3 | 18.9 | 14.2 | 0.21 |
| 65 | 35 | 120 | 20 | 41 | 21 | 33 | 1.3 | 18.2 | 14.3 | 0.21 |
| 75 | 25 | 120 | 20 | 40 | 21 | 32 | 1.2 | 17.4 | 14.3 | 0.21 |
| 85 | 15 | 120 | 20 | 39 | 20 | 31 | 1.2 | 16.7 | 14.4 | 0.21 |
| 95 | 5 | 120 | 20 | 37 | 20 | 30 | 1.1 | 16.0 | 14.6 | 0.21 |
| 100 | 0 | 120 | 20 | 36 | 20 | 29 | 1.1 | 15.7 | 14.6 | 0.21 |

Blowing Agents, Foams and Foamable Compositions

Typical "pour in place" foams were prepared by handmix. The polyol formulation (B-side) is made up of 100 parts of a polyol blend, 1.0 part by weight of N,N-dimethylcyclohexylamine, 0.3 parts by weight of N,N,N',N',N'',N''-pentamethyldiethylenetriamine, 1.9 parts by weight of a silicone surfactant (Tegostab® B 8465 sold by Evonik), 2 parts by weight of water and 13 parts by weight of a blowing agent blend consisting of HCFO-1233zd (E) and E-1,1,1,4,4,4-hexafluorobut-2-ene in a 50 wt %/50 wt % ratio.

The total B-side was prepared and mixed to 132 parts by weight of Desmodur 44V70L isocyanate. Good quality foams were obtained. The cell structure was fine and regular and the closed cells content was found higher than 95%.

The invention claimed is:

1. A foamable composition, wherein the foamable composition comprises a blowing agent and one or more components capable of reacting and foaming under conditions to form a foam or cellular structure,
    wherein the blowing agent comprises trans-1,1,1,4,4,4-hexafluoro-2-butene and 2-chloro-3,3,3-trifluoropropene.

2. The foamable composition according to claim 1, wherein the blowing agent comprises from 1 to 99% by weight of trans-1,1,1,4,4,4-hexafluoro-2-butene and from 1 to 99% by weight of 2-chloro-3,3,3-trifluoropropene.

3. The foamable composition according to claim 1, wherein the blowing agent comprises from 60 to 99% by weight of trans-1,1,1,4,4,4-hexafluoro-2-butene and from 1 to 40% by weight of 2-chloro-3,3,3-trifluoropropene.

4. A method of forming foam comprising reacting and foaming the foamable composition of claim 1 to form a foam.

5. A method of cleaning comprising applying a solvent on a surface and treating the surface, wherein the solvent comprises trans-1,1,1,4,4,4-hexafluoro-2-butene and 2-chloro-3,3,3-trifluoropropene.

6. The method of cleaning according to claim 5, wherein the solvent comprises from 1 to 99% by weight of trans-1,1,1,4,4,4-hexafluoro-2-butene and from 1 to 99% by weight of 2-chloro-3,3,3-trifluoropropene.

7. The method of cleaning according to claim 5, wherein the solvent comprises from 60 to 99% by weight of trans-1,1,1,4,4,4-hexafluoro-2-butene and from 1 to 40% by weight of 2-chloro-3,3,3-trifluoropropene.

8. A spray, wherein the spray comprises trans-1,1,1,4,4,4-hexafluoro-2-butene and 2-chloro-3,3,3-trifluoropropene, wherein the spray is formed by an aerosol.

9. A spray, wherein the spray comprises trans-1,1,1,4,4,4-hexafluoro-2-butene and 2-chloro-3,3,3-trifluoropropene, wherein the spray is selected from the group consisting of: deodorants, perfumes, hair sprays, cleansers, polishing agents, anti-asthma and anti-halitosis medications.

10. A heat transfer fluid, wherein the heat transfer fluid comprises trans-1,1,1,4,4,4-hexafluoro-2-butene, 2-chloro-3,3,3-trifluoropropene, and a lubricant.

11. The heat transfer fluid according to claim 10, wherein the lubricant is selected from the group consisting of: mineral oils, silicone oils, and polyalkylene glycol oils.

12. The heat transfer fluid according to claim 10, wherein the heat transfer fluid is configured for heat pumps operating at condensation temperature up to 140° C.

13. The heat transfer fluid according to claim 10, wherein the heat transfer fluid comprises from 1 to 99% by weight of trans-1,1,1,4,4,4-hexafluoro-2-butene and from 1 to 99% by weight of 2-chloro-3,3,3-trifluoropropene.

14. The heat transfer fluid according to claim 10, wherein the heat transfer fluid comprises from 60 to 99% by weight of trans-1,1,1,4,4,4-hexafluoro-2-butene and from 1 to 40% by weight of 2-chloro-3,3,3-trifluoropropene.

15. The heat transfer fluid according to claim 10, wherein the heat transfer fluid is azeotropic or azeotrope-like.

16. A heat transfer system comprising heat exchangers and a heat transfer fluid, wherein the heat exchangers include counterflow, counterflow-like, or cross-flow heat exchangers, and wherein the heat transfer fluid comprises trans-1,1,1,4,4,4-hexafluoro-2-butene and 2-chloro-3,3,3-trifluoropropene.

17. A composition comprising trans-1,1,1,4,4,4-hexafluoro-2-butene, 2-chloro-3,3,3-trifluoropropene, and at least one additive selected from the group consisting of stabilizers, metal passivators, and corrosion inhibitors.

18. A heat transfer system according to claim to claim 16, wherein the heat transfer fluid further comprises a lubricant.

19. A heat transfer system according to claim to claim 16, wherein the heat transfer fluid further comprises at least one additive selected from the group consisting of stabilizers, metal passivators, and corrosion inhibitors.

20. A sprayable composition including a propellant comprising trans-1,1,1,4,4,4-hexafluoro-2-butene and 2-chloro-3,3,3-trifluoropropene, wherein the sprayable composition is selected from the group consisting of: deodorants, perfumes, hair sprays, cleansers, polishing agents, anti-asthma medications and anti-halitosis medications.

21. A foamed thermoplastic comprising a polymer resin and a blowing agent, wherein the blowing agent comprises trans-1,1,1,4,4,4-hexafluoro-2-butene and 2-chloro-3,3,3-trifluoropropene.

22. The foamed thermoplastic according to claim 21, wherein the polymer resin comprises a polyol formulation.

23. The foamed thermoplastic according to claim 21, wherein the foamed thermoplastic further comprises a surfactant.

* * * * *